United States Patent
Nishimura

(10) Patent No.: US 10,172,925 B2
(45) Date of Patent: Jan. 8, 2019

(54) USES OF PARTIAL PEPTIDES OF SURVIVIN AND VARIATIONS THEREOF

(71) Applicant: Tella, Inc., Tokyo (JP)

(72) Inventor: Takashi Nishimura, Sapporo (JP)

(73) Assignee: Tella, Inc., Tokyo (JP)

( * ) Notice: Subject to any disclaimer, the term of this patent is extended or adjusted under 35 U.S.C. 154(b) by 0 days.

(21) Appl. No.: 15/003,959

(22) Filed: Jan. 22, 2016

(65) Prior Publication Data

US 2016/0193314 A1    Jul. 7, 2016

Related U.S. Application Data

(62) Division of application No. 12/935,761, filed as application No. PCT/JP2009/056649 on Mar. 31, 2009, now abandoned.

(30) Foreign Application Priority Data

Mar. 31, 2008 (JP) ................. 2008-093292

(51) Int. Cl.
| | | |
|---|---|---|
| A61K 39/00 | (2006.01) | |
| C07K 14/47 | (2006.01) | |
| C12N 5/0783 | (2010.01) | |
| A61K 38/00 | (2006.01) | |

(52) U.S. Cl.
CPC ...... *A61K 39/0011* (2013.01); *C07K 14/4747* (2013.01); *C07K 14/4748* (2013.01); *C12N 5/0636* (2013.01); *A61K 38/00* (2013.01); *A61K 39/00* (2013.01); *C12N 2501/998* (2013.01)

(58) Field of Classification Search
None
See application file for complete search history.

(56) References Cited

U.S. PATENT DOCUMENTS

| | | | |
|---|---|---|---|
| 6,245,523 B1 | 6/2001 | Altieri | |
| 6,992,063 B2 | 1/2006 | Shi | |
| 2004/0180354 A1 | 9/2004 | Simard et al. | |
| 2007/0104689 A1 | 5/2007 | Gillies et al. | |
| 2009/0004214 A1 | 1/2009 | Wang et al. | |

FOREIGN PATENT DOCUMENTS

| | | |
|---|---|---|
| JP | 2005/537800 | 12/2005 |
| JP | 2006/230269 | 7/2006 |
| JP | 2006/517529 | 7/2006 |
| WO | WO 1995/19783 | 1/1995 |
| WO | WO 1997/11669 | 9/1996 |
| WO | WO 2004/022709 | 9/2003 |
| WO | WO 2004/067023 | 1/2004 |
| WO | WO 2004/099389 A2 | 11/2004 |
| WO | WO 2007/036638 | 4/2007 |

OTHER PUBLICATIONS

Willingham et al. PNAS 109(7): 6662-6667, Apr. 24, 2012.*
"Guidance for Industry, Clinical Considerations for Therapeutic Cancer Vaccines," U.S. Department of Health and Human Services Food and Drug Administration Center for Biologics Evaluation and Research, Sep. 2009.
Bachinsky et al., Cancer Immunity, vol. 5, p. 6, pp. 1-9 (2005).
Blythe et al., Protein Science, 14:246-248 (2005).
Bodey et al, Anticancer Research, 20:2664-2676 (2000).
Bui et al., Immunogenetics, Jun. 2005,57(5);304-14. Epub May 3, 2005.
Caldas et al., *BioMed Central*, 4:1-9 (2005).
Casati, C., "The Apoptosis Inhibitor Protein Survivin Induces Tumor-specific CD8+ and CD4+ T Cells in Colorectal Cancer Patients", *Cancer Research*, (Aug. 1, 2003), vol. 63, pp. 4507-4515.
Celia Witten, Ph.D., M.D., "FDA and Cancer Vaccine Development," U.S. Food and Drug Administration Center for Biologics Evaluaiton and Research, Chicago, Illinois, Jun. 2, 2008.
Chamberlain et al., Expert Opinion on Pharmacotherapy 1(4):603-614 (2000).
Database GenBank Accession No. DQ508250.1 (2007).
Database GenBank Accession No. DQ508251.1 (2007).
Eisenhauer et al., European Journal of Cancer 45:228-247 (2009).
European Examination Report for International Appl. No. 09 729 061.3 dated May 14, 2013.
Fukuda et al., Mol. Cancer Ter. 5(5)1087-1098 (2006).
Gnjatic et al., PNAS 97(20):10917-10922 (2000).
Greenspan et al., Nature Biotechnology 17:936-937 (1999).
Hammer et al., Proc, Natl, Acad. Sci, USA, 91:4456-60 (1994).
Mahotka et al., Cancer Research, 59:6097-6102 (1999).
Mola et al., *J. Mol. Biol.*, 366:1055-1063 (2007).
Nielsen et al., BMC BioInformatics, 8:238 pp. 1-12 (2007).
Ohkuri, T. et al., "Identification of surviving helper epitopes and survivin-specific Th1 cells 34 applicable to human Th1 cell therapy", *Annual Meeting of the Japan Cancer Association*, (Sep. 2008), vol. 67th, p. 293.
Piesche, M. et al., "Identification of a promiscuous HLA DR-restricted T-cell epitope derived from the inhibitor of apoptosis protein surviving", *Human Immunology.*, (2007), vol. 68, pp. 572-576.
Singh and Raghava, Bioinformatics Applications Note, vol. 17, No. 12, pp. 1236-1237 (2001).

(Continued)

*Primary Examiner* — Alana Harris Dent
(74) *Attorney, Agent, or Firm* — RatnerPrestia

(57) ABSTRACT

The object aims to provide: a novel tumor antigen; a novel therapeutic agent useful in a method for treating a malignant neoplasm by utilizing the tumor antigen; and a tumor antigen which can be used as the therapeutic agent. Thus, disclosed are: a novel tumor antigen which has an epitope capable of inducing a Th1 cell which is a CD4-positive T cell specific to Survivin; and use of the tumor antigen. Specifically disclosed is a polypeptide which comprises an amino acid sequence depicted in SEQ ID NO:17 or the like and has an activity to cause the production of a cytokine by a Th cell that is a cell specific to Survivin. The peptide can induce a Th cell that is specific to Survivin and can cause the production of a cytokine by the Sur/Th cell when the peptide is incubated together with an antigen-presenting cell and a CD4-positive T cell.

12 Claims, 10 Drawing Sheets

Specification includes a Sequence Listing.

(56) References Cited

OTHER PUBLICATIONS

Topalian, S. et al., "Human CD4+ T cells specifically recognize a shared melanoma-associated antigen encoded by the tyrosinase gene", *Proc. Natl. Acad. Sci. USA*, (1994), vol. 91, pp. 9461-9465.
Uenaka et al., *Cancer Immunity* 7:9 (2007).
Uniport A3E0Z9, Version 16 dated May 29, 2013.
Uniport A3E100, Version 16 dated May 29, 2013.
Wang et al., PLoS Computational Biology, vol. 4, Issue 4, pp. 1-10 (2008).
Wang, Y.F. et al., "Comprehensive analysis of HLA-DR- and HLA-DP4-restricted CD4+ T cell response specific for the tumor-shared antigen surviving in healthy donors and cancer patients", *J. Immunology*, (Jul. 2008), vol. 181, No. 1, pp. 431-439.

* cited by examiner

SEQUENCE LISTING

<160> NUMBER OF SEQ ID NOS: 57

<210> SEQ ID NO 1
<211> LENGTH: 20
<212> TYPE: PRT
<213> ORGANISM: Homo sapiens

<400> SEQUENCE: 1

Met Gly Ala Pro Thr Leu Pro Pro Ala Trp Gln Pro Phe Leu Lys Asp
1               5                   10                  15

His Arg Ile Ser
            20

<210> SEQ ID NO 2
<211> LENGTH: 20
<212> TYPE: PRT
<213> ORGANISM: Homo sapiens

<400> SEQUENCE: 2

Pro Ala Trp Gln Pro Phe Leu Lys Asp His Arg Ile Ser Thr Phe Lys
1               5                   10                  15

-continued

Asn Trp Pro Phe
            20

<210> SEQ ID NO 3
<211> LENGTH: 19
<212> TYPE: PRT
<213> ORGANISM: Homo sapiens

<400> SEQUENCE: 3

Leu Lys Asp His Arg Ile Ser Thr Phe Lys Asn Trp Pro Phe Leu Glu
1               5                   10                  15

Gly Cys Ala

<210> SEQ ID NO 4
<211> LENGTH: 20
<212> TYPE: PRT
<213> ORGANISM: Homo sapiens

<400> SEQUENCE: 4

Phe Lys Asn Trp Pro Phe Leu Glu Gly Cys Ala Cys Thr Pro Glu Arg
1               5                   10                  15

Met Ala Glu Ala
            20

<210> SEQ ID NO 5
<211> LENGTH: 19
<212> TYPE: PRT
<213> ORGANISM: Homo sapiens

<400> SEQUENCE: 5

Glu Gly Cys Ala Cys Thr Pro Glu Arg Met Ala Glu Ala Gly Phe Ile
1               5                   10                  15

His Cys Pro

<210> SEQ ID NO 6
<211> LENGTH: 20
<212> TYPE: PRT
<213> ORGANISM: Homo sapiens

<400> SEQUENCE: 6

Pro Glu Arg Met Ala Glu Ala Gly Phe Ile His Cys Pro Thr Glu Asn
1               5                   10                  15

Glu Pro Asp Leu
            20

<210> SEQ ID NO 7
<211> LENGTH: 17
<212> TYPE: PRT
<213> ORGANISM: Homo sapiens

<400> SEQUENCE: 7

Gly Phe Ile His Cys Pro Thr Glu Asn Glu Pro Asp Leu Ala Gln Cys
1               5                   10                  15

Phe

<210> SEQ ID NO 8
<211> LENGTH: 19
<212> TYPE: PRT
<213> ORGANISM: Homo sapiens

<400> SEQUENCE: 8

Pro Thr Glu Asn Glu Pro Asp Leu Ala Gln Cys Phe Phe Cys Phe Lys
1               5                   10                  15

Glu Leu Glu

<210> SEQ ID NO 9
<211> LENGTH: 18
<212> TYPE: PRT
<213> ORGANISM: Homo sapiens

<400> SEQUENCE: 9

Asp Leu Ala Gln Cys Phe Phe Cys Phe Lys Glu Leu Glu Gly Trp Glu
1               5                   10                  15

Pro Asp

<210> SEQ ID NO 10
<211> LENGTH: 18
<212> TYPE: PRT
<213> ORGANISM: Homo sapiens

<400> SEQUENCE: 10

Phe Phe Cys Phe Lys Glu Leu Glu Gly Trp Glu Pro Asp Asp Pro
1               5                   10                  15

Ile Gly

<210> SEQ ID NO 11
<211> LENGTH: 20
<212> TYPE: PRT
<213> ORGANISM: Homo sapiens

<400> SEQUENCE: 11

Glu Leu Glu Gly Trp Glu Pro Asp Asp Pro Ile Gly Pro Gly Thr
1               5                   10                  15

Val Ala Tyr Ala
            20

<210> SEQ ID NO 12
<211> LENGTH: 20
<212> TYPE: PRT
<213> ORGANISM: Homo sapiens

<400> SEQUENCE: 12

Asp Asp Asp Pro Ile Gly Pro Gly Thr Val Ala Tyr Ala Cys Asn Thr
1               5                   10                  15

Ser Thr Leu Gly
            20

<210> SEQ ID NO 13
<211> LENGTH: 17
<212> TYPE: PRT
<213> ORGANISM: Homo sapiens

<400> SEQUENCE: 13

Gly Thr Val Ala Tyr Ala Cys Asn Thr Ser Thr Leu Gly Gly Arg Gly
1               5                   10                  15

Gly

<210> SEQ ID NO 14
<211> LENGTH: 18
<212> TYPE: PRT
<213> ORGANISM: Homo sapiens

<400> SEQUENCE: 14

Asn Thr Ser Thr Leu Gly Gly Arg Gly Gly Arg Ile Thr Arg Glu Glu
1               5                   10                  15

His Lys

<210> SEQ ID NO 15
<211> LENGTH: 16
<212> TYPE: PRT
<213> ORGANISM: Homo sapiens

<400> SEQUENCE: 15

Gly Gly Arg Gly Gly Arg Ile Thr Arg Glu Glu His Lys Lys His Ser
1               5                   10                  15

<210> SEQ ID NO 16
<211> LENGTH: 17
<212> TYPE: PRT
<213> ORGANISM: Homo sapiens

<400> SEQUENCE: 16

Arg Ile Thr Arg Glu Glu His Lys Lys His Ser Ser Gly Cys Ala Phe
1               5                   10                  15

Leu

<210> SEQ ID NO 17
<211> LENGTH: 19
<212> TYPE: PRT
<213> ORGANISM: Homo sapiens

<400> SEQUENCE: 17

Glu His Lys Lys His Ser Ser Gly Cys Ala Phe Leu Ser Val Lys Lys
1               5                   10                  15

Gln Phe Glu

<210> SEQ ID NO 18
<211> LENGTH: 19
<212> TYPE: PRT
<213> ORGANISM: Homo sapiens

<400> SEQUENCE: 18

Gly Cys Ala Phe Leu Ser Val Lys Lys Gln Phe Glu Glu Leu Thr Leu
1               5                   10                  15

Gly Glu Phe

<210> SEQ ID NO 19
<211> LENGTH: 20
<212> TYPE: PRT
<213> ORGANISM: Homo sapiens

<400> SEQUENCE: 19

Val Lys Lys Gln Phe Glu Glu Leu Thr Leu Gly Glu Phe Leu Lys Leu
1               5                   10                  15

Asp Arg Glu Arg
            20

<210> SEQ ID NO 20
<211> LENGTH: 20
<212> TYPE: PRT
<213> ORGANISM: Homo sapiens

<400> SEQUENCE: 20

Leu Thr Leu Gly Glu Phe Leu Lys Leu Asp Arg Glu Arg Ala Lys Asn

```
1               5                   10                  15

Lys Ile Ala Lys
            20

<210> SEQ ID NO 21
<211> LENGTH: 20
<212> TYPE: PRT
<213> ORGANISM: Homo sapiens

<400> SEQUENCE: 21

Lys Leu Asp Arg Glu Arg Ala Lys Asn Lys Ile Ala Lys Glu Thr Asn
1               5                   10                  15

Asn Lys Lys Lys
            20

<210> SEQ ID NO 22
<211> LENGTH: 20
<212> TYPE: PRT
<213> ORGANISM: Homo sapiens

<400> SEQUENCE: 22

Lys Asn Lys Ile Ala Lys Glu Thr Asn Asn Lys Lys Lys Glu Phe Glu
1               5                   10                  15

Glu Thr Ala Lys
            20

<210> SEQ ID NO 23
<211> LENGTH: 20
<212> TYPE: PRT
<213> ORGANISM: Homo sapiens

<400> SEQUENCE: 23

Thr Asn Asn Lys Lys Lys Glu Phe Glu Glu Thr Ala Lys Lys Val Arg
1               5                   10                  15

Arg Ala Ile Glu
            20

<210> SEQ ID NO 24
<211> LENGTH: 17
<212> TYPE: PRT
<213> ORGANISM: Homo sapiens

<400> SEQUENCE: 24

Glu Phe Glu Glu Thr Ala Lys Lys Val Arg Arg Ala Ile Glu Gln Leu
1               5                   10                  15

Ala

<210> SEQ ID NO 25
<211> LENGTH: 15
<212> TYPE: PRT
<213> ORGANISM: Homo sapiens

<400> SEQUENCE: 25

Ala Lys Lys Val Arg Arg Ala Ile Glu Gln Leu Ala Ala Met Asp
1               5                   10                  15

<210> SEQ ID NO 26
<211> LENGTH: 12
<212> TYPE: PRT
<213> ORGANISM: Homo sapiens

<400> SEQUENCE: 26
```

```
Glu His Lys Lys His Ser Ser Gly Cys Ala Phe Leu
1               5                   10
```

<210> SEQ ID NO 27
<211> LENGTH: 13
<212> TYPE: PRT
<213> ORGANISM: Homo sapiens

<400> SEQUENCE: 27

```
Glu His Lys Lys His Ser Ser Gly Cys Ala Phe Leu Ser
1               5                   10
```

<210> SEQ ID NO 28
<211> LENGTH: 14
<212> TYPE: PRT
<213> ORGANISM: Homo sapiens

<400> SEQUENCE: 28

```
Glu His Lys Lys His Ser Ser Gly Cys Ala Phe Leu Ser Val
1               5                   10
```

<210> SEQ ID NO 29
<211> LENGTH: 15
<212> TYPE: PRT
<213> ORGANISM: Homo sapiens

<400> SEQUENCE: 29

```
Glu His Lys Lys His Ser Ser Gly Cys Ala Phe Leu Ser Val Lys
1               5                   10                  15
```

<210> SEQ ID NO 30
<211> LENGTH: 15
<212> TYPE: PRT
<213> ORGANISM: Homo sapiens

<400> SEQUENCE: 30

```
His Lys Lys His Ser Ser Gly Cys Ala Phe Leu Ser Val Lys Lys
1               5                   10                  15
```

<210> SEQ ID NO 31
<211> LENGTH: 15
<212> TYPE: PRT
<213> ORGANISM: Homo sapiens

<400> SEQUENCE: 31

```
Lys Lys His Ser Ser Gly Cys Ala Phe Leu Ser Val Lys Lys Gln
1               5                   10                  15
```

<210> SEQ ID NO 32
<211> LENGTH: 15
<212> TYPE: PRT
<213> ORGANISM: Homo sapiens

<400> SEQUENCE: 32

```
Lys His Ser Ser Gly Cys Ala Phe Leu Ser Val Lys Lys Gln Phe
1               5                   10                  15
```

<210> SEQ ID NO 33
<211> LENGTH: 15
<212> TYPE: PRT
<213> ORGANISM: Homo sapiens

<400> SEQUENCE: 33

```
His Ser Ser Gly Cys Ala Phe Leu Ser Val Lys Lys Gln Phe Glu
1               5                   10                  15
```

<210> SEQ ID NO 34
<211> LENGTH: 14
<212> TYPE: PRT
<213> ORGANISM: Homo sapiens

<400> SEQUENCE: 34

Ser Ser Gly Cys Ala Phe Leu Ser Val Lys Lys Gln Phe Glu
1               5                   10

<210> SEQ ID NO 35
<211> LENGTH: 13
<212> TYPE: PRT
<213> ORGANISM: Homo sapiens

<400> SEQUENCE: 35

Ser Gly Cys Ala Phe Leu Ser Val Lys Lys Gln Phe Glu
1               5                   10

<210> SEQ ID NO 36
<211> LENGTH: 12
<212> TYPE: PRT
<213> ORGANISM: Homo sapiens

<400> SEQUENCE: 36

Gly Cys Ala Phe Leu Ser Val Lys Lys Gln Phe Glu
1               5                   10

<210> SEQ ID NO 37
<211> LENGTH: 10
<212> TYPE: PRT
<213> ORGANISM: Homo sapiens

<400> SEQUENCE: 37

Gly Cys Ala Phe Leu Ser Val Lys Lys Gln
1               5                   10

<210> SEQ ID NO 38
<211> LENGTH: 19
<212> TYPE: PRT
<213> ORGANISM: Homo sapiens

<400> SEQUENCE: 38

Ala His Lys Lys His Ser Ser Gly Cys Ala Phe Leu Ser Val Lys Lys
1               5                   10                  15

Gln Phe Glu

<210> SEQ ID NO 39
<211> LENGTH: 19
<212> TYPE: PRT
<213> ORGANISM: Homo sapiens

<400> SEQUENCE: 39

Glu Ala Lys Lys His Ser Ser Gly Cys Ala Phe Leu Ser Val Lys Lys
1               5                   10                  15

Gln Phe Glu

<210> SEQ ID NO 40
<211> LENGTH: 19
<212> TYPE: PRT
<213> ORGANISM: Homo sapiens

<400> SEQUENCE: 40

Glu His Ala Lys His Ser Ser Gly Cys Ala Phe Leu Ser Val Lys Lys
1               5                   10                  15

Gln Phe Glu

<210> SEQ ID NO 41
<211> LENGTH: 19
<212> TYPE: PRT
<213> ORGANISM: Homo sapiens

<400> SEQUENCE: 41

Glu His Lys Ala His Ser Ser Gly Cys Ala Phe Leu Ser Val Lys Lys
1               5                   10                  15

Gln Phe Glu

<210> SEQ ID NO 42
<211> LENGTH: 19
<212> TYPE: PRT
<213> ORGANISM: Homo sapiens

<400> SEQUENCE: 42

Glu His Lys Lys Ala Ser Ser Gly Cys Ala Phe Leu Ser Val Lys Lys
1               5                   10                  15

Gln Phe Glu

<210> SEQ ID NO 43
<211> LENGTH: 19
<212> TYPE: PRT
<213> ORGANISM: Homo sapiens

<400> SEQUENCE: 43

Glu His Lys Lys His Ala Ser Gly Cys Ala Phe Leu Ser Val Lys Lys
1               5                   10                  15

Gln Phe Glu

<210> SEQ ID NO 44
<211> LENGTH: 19
<212> TYPE: PRT
<213> ORGANISM: Homo sapiens

<400> SEQUENCE: 44

Glu His Lys Lys His Ser Ala Gly Cys Ala Phe Leu Ser Val Lys Lys
1               5                   10                  15

Gln Phe Glu

<210> SEQ ID NO 45
<211> LENGTH: 19
<212> TYPE: PRT
<213> ORGANISM: Homo sapiens

<400> SEQUENCE: 45

Glu His Lys Lys His Ser Ser Ala Cys Ala Phe Leu Ser Val Lys Lys
1               5                   10                  15

Gln Phe Glu

<210> SEQ ID NO 46
<211> LENGTH: 19
<212> TYPE: PRT
<213> ORGANISM: Homo sapiens

<400> SEQUENCE: 46

Glu His Lys Lys His Ser Ser Gly Gly Ala Phe Leu Ser Val Lys Lys

```
            1               5                  10                  15

Gln Phe Glu

<210> SEQ ID NO 47
<211> LENGTH: 19
<212> TYPE: PRT
<213> ORGANISM: Homo sapiens

<400> SEQUENCE: 47

Glu His Lys Lys His Ser Ser Gly Cys Gly Phe Leu Ser Val Lys Lys
1               5                   10                  15

Gln Phe Glu

<210> SEQ ID NO 48
<211> LENGTH: 19
<212> TYPE: PRT
<213> ORGANISM: Homo sapiens

<400> SEQUENCE: 48

Glu His Lys Lys His Ser Ser Gly Cys Ala Gly Leu Ser Val Lys Lys
1               5                   10                  15

Gln Phe Glu

<210> SEQ ID NO 49
<211> LENGTH: 19
<212> TYPE: PRT
<213> ORGANISM: Homo sapiens

<400> SEQUENCE: 49

Glu His Lys Lys His Ser Ser Gly Cys Ala Phe Ala Ser Val Lys Lys
1               5                   10                  15

Gln Phe Glu

<210> SEQ ID NO 50
<211> LENGTH: 19
<212> TYPE: PRT
<213> ORGANISM: Homo sapiens

<400> SEQUENCE: 50

Glu His Lys Lys His Ser Ser Gly Cys Ala Phe Leu Ala Val Lys Lys
1               5                   10                  15

Gln Phe Glu

<210> SEQ ID NO 51
<211> LENGTH: 19
<212> TYPE: PRT
<213> ORGANISM: Homo sapiens

<400> SEQUENCE: 51

Glu His Lys Lys His Ser Ser Gly Cys Ala Phe Leu Ser Ala Lys Lys
1               5                   10                  15

Gln Phe Glu

<210> SEQ ID NO 52
<211> LENGTH: 19
<212> TYPE: PRT
<213> ORGANISM: Homo sapiens

<400> SEQUENCE: 52

Glu His Lys Lys His Ser Ser Gly Cys Ala Phe Leu Ser Val Ala Lys
1               5                   10                  15
```

Gln Phe Glu

<210> SEQ ID NO 53
<211> LENGTH: 19
<212> TYPE: PRT
<213> ORGANISM: Homo sapiens

<400> SEQUENCE: 53

Glu His Lys Lys His Ser Ser Gly Cys Ala Phe Leu Ser Val Lys Ala
1               5                   10                  15

Gln Phe Glu

<210> SEQ ID NO 54
<211> LENGTH: 19
<212> TYPE: PRT
<213> ORGANISM: Homo sapiens

<400> SEQUENCE: 54

Glu His Lys Lys His Ser Ser Gly Cys Ala Phe Leu Ser Val Lys Lys
1               5                   10                  15

Ala Phe Glu

<210> SEQ ID NO 55
<211> LENGTH: 19
<212> TYPE: PRT
<213> ORGANISM: Artificial Sequence
<220> FEATURE:
<223> OTHER INFORMATION: antigen epitope of the sequence No.17 (SU18)
      to HLA-DQB1*0601
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(19)
<223> OTHER INFORMATION: Xaa can be any naturally occurring amino acid

<400> SEQUENCE: 55

Xaa Xaa Xaa Lys His Xaa Ser Xaa Cys Xaa Xaa Xaa Xaa Xaa Xaa Xaa
1               5                   10                  15

Xaa Xaa Xaa

<210> SEQ ID NO 56
<211> LENGTH: 165
<212> TYPE: PRT
<213> ORGANISM: Homo sapiens

<400> SEQUENCE: 56

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
                20                  25                  30

Cys Thr Pro Glu Arg Met Ala Glu Ala Gly Phe Ile His Cys Pro Thr
            35                  40                  45

Glu Asn Glu Pro Asp Leu Ala Gln Cys Phe Phe Cys Phe Lys Glu Leu

```
                50                  55                  60
Glu Gly Trp Glu Pro Asp Asp Pro Ile Gly Pro Gly Thr Val Ala
 65                  70                  75                  80

Tyr Ala Cys Asn Thr Ser Thr Leu Gly Gly Arg Gly Gly Arg Ile Thr
                 85                  90                  95

Arg Glu Glu His Lys Lys His Ser Ser Gly Cys Ala Phe Leu Ser Val
                100                 105                 110

Lys Lys Gln Phe Glu Glu Leu Thr Leu Gly Glu Phe Leu Lys Leu Asp
                115                 120                 125

Arg Glu Arg Ala Lys Asn Lys Ile Ala Lys Glu Thr Asn Asn Lys Lys
            130                 135                 140

Lys Glu Phe Glu Glu Thr Ala Lys Lys Val Arg Arg Ala Ile Glu Gln
145                 150                 155                 160

Leu Ala Ala Met Asp
                165

<210> SEQ ID NO 57
<211> LENGTH: 11
<212> TYPE: PRT
<213> ORGANISM: Homo sapiens

<400> SEQUENCE: 57

Lys His Ser Ser Gly Cys Ala Phe Leu Ser Val
 1               5                  10
```

USES OF PARTIAL PEPTIDES OF SURVIVIN AND VARIATIONS THEREOF

CROSS REFERENCE TO RELATED APPLICATIONS

This application is a divisional of U.S. application Ser. No. 12/935,761, filed Sep. 30, 2010, which is the U.S. national stage of International Application No. PCT/JP2009/056649, filed Mar. 31, 2009, which claims priority to Japanese Application No. 2008-093292, filed Mar. 31, 2008, the contents of each of which are incorporated by reference in their entireties.

FIELD OF THE INVENTION

The present invention relates to an antigenic polypeptide that can be used in cancer immunotherapy and to a therapeutic agent for malignant neoplasms comprising the polypeptide.

BACKGROUND OF THE INVENTION

One of the therapeutic methods for cancers (malignant neoplasms), an intractable disease, includes so-called cancer immunotherapy which causes regression of cancer cells by utilizing an immune system of individual patients. The important point in this method is how to make the immune system recognize the cancer cells as foreign and induce immune cells that are aggressive to the cancer cells.

Key immune cells involved in antitumor immunity include a cytotoxic T cell expressing cell surface protein CD8 (CD8-positive T cell) and a T cell expressing cell surface protein CD4 (CD4-positive T cell). CD8-positive T cells are those that, when activated, lyse a cell presenting antigens bound to an HLA class I molecule. CD4-positive T cells are cytokine-secreting Th cells, which, upon being activated by macrophages and/or dendritic cells which present antigens on HLA class II molecules, exert a helper function for inducing and maintaining CD8-positive T cells.

Th cells are known to be classified by the type of cytokine that they secrete into Th1 cells (producing IFN-γ or the like), Th2 cells (producing IL-4 or the like), and Th0 cells (having a low cytokine-producing ability or producing both IFN-γ and IL-4), and the roles of each cell are now being elucidated. CD4-positive T cells can be provided with an effector function by their indirect mechanism against MHC class II molecule-negative tumors (MHC class II-tumors) via, for example, activation of macrophages or by their direct mechanism against MHC class II-positive tumors.

Previous studies of T cells in human cancer immunotherapy have mainly focused on identification and induction of CD8-positive HLA class I restricted CTL response (Patent Document 1). As for CD4-positive T cells, tyrosinase, a cancer antigen; the identification of its epitope to CD4-positive T cells; and some other epitopes have been reported (Patent Document 2), but the number of reports on CD4-positive T cells is much smaller than that on CD8-positive HLA class I restricted peptide.

Reported tyrosinase, which is expressed in normal and tumor cells of the melanocyte lineage and shown to be a specific target of CD4-positive melanoma-reactive T cells, is the only melanoma-associated and tissue-specific antigen that binds to MHC class II molecules (Non-Patent Document 1). However, since tyrosinase is expressed only in limited types of tumors, it can hardly be said to be a promising cancer antigen in cancer immunotherapy.

A gene, referred to as Survivin, which encodes tumor-specific antigens that can be recognized by CD8-positive T cells has recently been reported (Non-Patent Document 2). Survivin is a 142-amino acid residue protein identified as a substance that inhibits apoptotic action. It has been reported that Survivin is distinctively characterized by its upregulated expression in limited normal tissues such as fetal tissues, and thymus and testis of adult; and in tumor tissues, particularly tumorigenic lung, colon, mammary gland, spleen, prostate gland, and lymphoma (Non-Patent Document 2).

Survivin, upregulated expression of which has also been reported to correlate with poor prognosis of neoplastic diseases, is considered to be a protein that plays a very important role as a tumor antigen, and the identification of MHC class II restricted peptide in Survivin has been carried out (Non-Patent Document 3). However, since the peptide reported in Non-Patent Document 3 restricts limited HLA types of HLA class II, it is necessary to use multiple peptides, which are applicable to more HLA types, to be clinically available.

Non-Patent Document 1
Topalian, S. L. et al., 1994, Proc. Natl. Acad. Sci. USA, Vol. 91, pp. 9461-9465
Non-Patent Document 2
Chiara Casati et al., CANCER RESEARCH, 2003, Vol. 63, pp. 4507-4515
Non-Patent Document 3
Matthias Piesche et al., Human Immunology, 2007, Vol. 68, pp. 572-576
Patent Document 1
WO95/19783
Patent Document 2
WO97/11669

SUMMARY OF THE INVENTION

The present invention provides a novel tumor antigen, a novel therapeutic agent useful in the method of treating malignant neoplasms by using the tumor antigen, and a tumor antigen that can be used in the therapeutic agent.

Means for Solving the Problems

The present inventors experimentally found that a therapeutic agent containing tumor antigens and Th cells specific to the tumor antigens has an effect of causing a significant regression of malignant neoplasms expressing the tumor antigens, and further identified a novel antigenic peptide that can be used as the tumor antigens, thereby completing each of the following inventions.

(1) A polypeptide, comprising any of the amino acid sequences a) to g) below and having an activity to produce cytokines in Th cells specific to Survivin:
a) An amino acid sequence represented by SEQ ID NO:17;
b) An amino acid sequence in which one to several tens of any amino acids are added to the N terminus and/or C terminus of the amino acid sequence represented by SEQ ID No:17;
c) An amino acid sequence in which one to four amino acids at the N terminus of the amino acid sequence represented by SEQ ID No:17 are deleted;
d) An amino acid sequence in which one to five amino acids at the C terminus of the amino acid sequence represented by SEQ ID No:17 are deleted;
e) An amino acid sequence in which one to several amino acid residues of the amino acid sequence represented by SEQ ID No:17 are substituted and/or deleted;

f) An amino acid sequence in which one to several tens of any amino acids are added to the N terminus and/or C terminus of an amino acid sequence in which one to several amino acid residues of the amino acid sequence represented by SEQ ID No:17 are substituted and/or deleted; and g) An amino acid sequence in which one to five amino acids at the N terminus and/or C terminus of the amino acid sequence represented by SEQ ID No:17 are deleted, wherein one to several amino acid residues are further substituted.

(2) The polypeptide according to (1), wherein a polypeptide comprising amino acid sequences b) to g) has an epitope of a polypeptide comprising the amino acid sequence represented by SEQ ID No:17, the epitope inducing Th cells specific to Survivin from CD4-positive T cells.

(3) A nucleic acid encoding the polypeptide according to (1) or (2).

(4) A vector comprising the nucleic acid according to (3).

(5) An antibody that specifically binds to the polypeptide according to (1) or (2).

(6) A vaccine for immunotherapy for malignant neoplasms, comprising at least one of the polypeptides according to (1) and (2) as an active ingredient.

(7) A method for inducing Th cells specific to Survivin, comprising a process for incubating in vitro at least one of the polypeptides according to (1) and (2), antigen-presenting cells and CD4-positive T cells.

(8) A therapeutic agent for malignant neoplasms, comprising the polypeptide according to (1) or (2) and Th cells specific to the polypeptide or Survivin.

Advantages of the Invention

The peptide of the present invention induces Th cells specific to Survivin (hereinafter referred to as Sur/Th cells) by incubating the peptide with antigen-presenting cells and CD4-positive T cells and has an activity to produce cytokines in the Sur/Th cells. Since the Sur/Th cells specifically attacks the malignant neoplasms expressing Survivin, the peptide of the present invention can be used as an ingredient of a therapeutic agent for malignant neoplasms.

Since the polypeptide of the present invention, having a small number of constituent amino acid residues, can be produced in large quantities not only by gene recombination techniques but also by organic synthetic methods, the polypeptide can be supplied in clinical studies and applications stably and inexpensively.

A therapeutic agent for malignant neoplasms comprising the polypeptide of the present invention, by combining tumor antigens with Th cells specific to the tumor antigens, can more strongly promote the production of cytokines in the Th cells. The cytokines produced induce in vivo antitumor immune response specific to the malignant neoplasms expressing the tumor antigens to cause regression of the tumor.

DETAILED DESCRIPTION OF THE INVENTION

Figure 1:
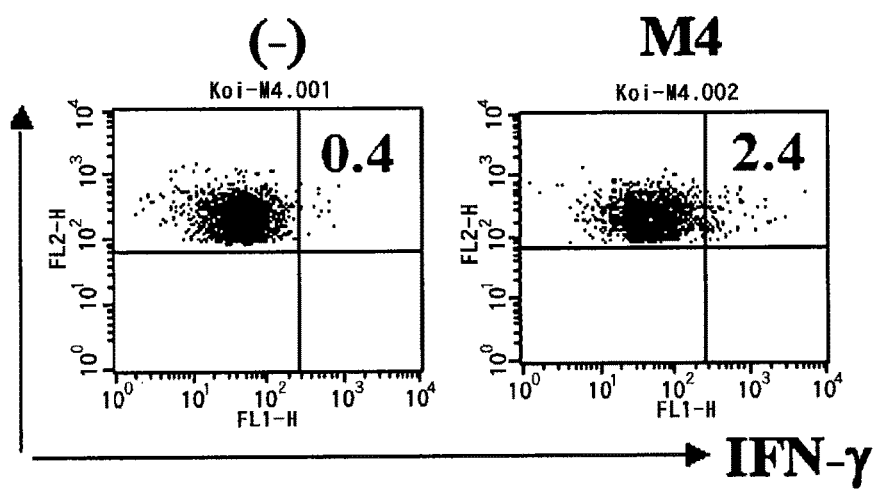
FIG. 1 shows the results of the intracellular staining showing the measurements of the production of INF-γ by Sur/Th cells where each of the mixed peptides MIX1 to MIX5 was added to the group of cells comprising the Sur/Th cells induced from a human whose HLA genotype is HLA-DRB1*0101/HLA-DRB1*0901. In the figure, the ordinate indicates the CD4 expression level and the abscissa the INF-γ expression level.

The present invention relates to a partial polypeptide of Survivin, a tumor antigen comprising the partial polypeptide, and a therapeutic agent for malignant neoplasms comprising the tumor antigen and Th cells specific to the tumor antigen. This invented therapeutic agent for malignant neoplasms is the therapeutic agent preferably comprising tumor antigen comprising partial polypeptide of Survivin and cognate tumor antigen-specific Th cells induced from CD4-positive T cells of patient to be treated.

Because this invented therapeutic agent for malignant neoplasms comprises tumor antigens, a partial polypeptide of Survivin, in combination with Th cells specific to the tumor antigens, the agent exerts a significant effect in regression of malignant neoplasms compared to the case where the tumor antigens or the Th cells specific to the tumor antigens are separately administered to a patient.

Th cells specific to the tumor antigens comprising a partial polypeptide of Survivin may be any of Th0 cells, Th1 cells, or Th2 cells as long as they are Th cells that produce cytokines by specific stimulation by the tumor antigens, and more preferably Th1 cell. Th cells specific to such tumor antigens can be induced and prepared from the CD4-positive T cells by incubating the tumor antigens, antigen-presenting cells expressing HLA class II molecules, and the CD4-positive T cells under appropriate conditions.

CD4-positive T cells that can be used in the method of the present invention can be isolated from the collected blood by common methods, for example, a method using MACS (Miltenyi Biotech) or the like. In the present invention, CD4-positive T cells collected from a patient with malignant neoplasms to be treated are preferably used.

Antigen-presenting cells that can be used in the method of the present invention may be any cell expressing HLA class II molecules on their surface, examples of which include B cell, macrophage, monocyte and non-proliferative transfectant as well as dendritic cell, but are not limited thereto.

As for incubation, tumor antigens comprising a partial polypeptide of Survivin, antigen-presenting cells, and CD4-positive T cells may be simultaneously incubated, or after the tumor antigens and the antigen-presenting cells are incubated, they may be incubated together with the CD4-positive T cells. The incubation may be carried out under the conditions in accordance with a common method by which, in the presence of IL-2, the desired antigen is presented by the antigen-presenting cells via HLA Class II molecules and mature Th cells specific to the antigen are induced from CD4-positive T cells, e.g., the method described in Tim et al., (Immunology Today, 1996, Vol. 17, No. 3, pp. 138-146). On the basis of the descriptions by Nishimura et al., (J. Exp. Med., 1999, Vol. 190, No. 5, pp. 617-627), any of Th0 cells, Th1 cells, or Th2 cells can be specifically induced from CD4-positive T cells by changing incubation conditions variously.

The induction of Th0 cells, Th1 cells, or Th2 cells can be confirmed by observing cytokines in each cell produced when the cell was restimulated with a tumor antigen, a partial polypeptide of Survivin (e.g., Tim et al., mentioned above). Cytokine production can be confirmed, using ELISA, intracellular staining, ELISPOT, and other various methods.

One aspect of the polypeptide of the present invention is an antigen polypeptide corresponding to an amino acid sequence of NO. 76 to 94 of a tumor antigen protein (the above Non-Patent Document 2) (SEQ ID NO:17, hereinafter referred to as SU18), referred to as Survivin.

In addition, polypeptides comprising the amino acid sequences having such relations as b) to g) below with the amino acid sequences of the polypeptide, SU18 (SEQ ID NO:17), also can be used as the tumor antigen of the present invention.

b) An amino acid sequence in which one to several tens of any amino acids are added to the N terminus and/or C terminus of the amino acid sequence represented by SEQ ID No:17;

c) An amino acid sequence in which one to four amino acids at the N terminus of the amino acid sequence represented by SEQ ID No:17 are deleted;

d) An amino acid sequence in which one to five amino acids at the C terminus of the amino acid sequence represented by SEQ ID No:17 are deleted;

e) An amino acid sequence in which one to several amino acid residues of the amino acid sequence represented by SEQ ID No:17 are substituted and/or deleted;

f) An amino acid sequence in which one to several tens of any amino acids are added to the N terminus and/or C terminus of the amino acid sequence in which one to several amino acid residues of the amino acid sequence represented by SEQ ID No:17 are substituted and/or deleted; and g) An amino acid sequence in which one to five amino acids at the N terminus and/or C terminus of the amino acid sequence represented by SEQ ID No:17 are deleted, wherein one to several amino acid residues are further substituted.

The amino acid sequences of b) to g) described above are defined as an amino acid sequence constituting a polypeptide that retains epitopes existing in SU18 and has an activity to produce cytokines in Sur/Th cells, or that has epitopes that induces Th cells specific to Survivin or SU18 from CD4-positive T cells.

Although amino acid residues that are substituted, deleted, or added, as defined in b) to g), are not particularly limited within a range where the activities or functions of the polypeptide described above are maintained, addition of one to several tens of amino acids in b) and f) means addition of 1 to 50 amino acids, preferably 1 to 30 amino acids, and more preferably 1 to 15 amino acids.

Preferred examples of the substitution, deletion, or addition of the amino acid as described above are silent substitution, deletion, and addition; especially preferred is conservative amino acid substitution. These examples do not change an activity to produce cytokines in the Sur/Th cells of the polypeptide in the present invention or epitopes that induce Th cells specific to Survivin or SU18 from CD4-positive T cells. Typical examples of the conservative substitution include mutual substitution of hydrophobic amino acids, Ala, Val, Leu, and Ile; mutual substitution of hydroxyl amino acids, Ser and Thr; mutual substitution of acidic residues, Asp and Glu; mutual substitution of amide type amino acids, Asn and Gln; mutual substitution of basic amino acids, Lys and Arg; and mutual substitution of aromatic amino acids, Phe and Tyr.

SU18 has an activity to produce cytokines in Sur/Th cells induced from CD4-positive T cells by incubating Survivin, antigen-presenting cells, and CD4-positive T cells, meaning that SU18 has epitopes that can be recognized by the Sur/Th cells and the epitopes are presented by MHC class II molecules expressing on the surface of antigen-presenting cells in which Survivin is taken up. Therefore, a therapeutic agent for malignant neoplasms comprising Survivin, SU18, and Sur/Th cells is one aspect of the present invention. A therapeutic agent for malignant neoplasms, comprising Th cells specific to SU18 induced from CD4-positive T cells by incubating Survivin and/or SU18, antigen-presenting cells, and the CD4-positive T cells, is also one aspect of the present invention.

SU18 is believed to be a polypeptide that can be a tumor antigen not only in human having HLA genotype of HLA-DRB1*0101 but also in human whose HLA genotype is HLA-DRB1*1201/HLA-DRB1*1502 or HLA-DQB1*0601.

Every polypeptide described above is a novel polypeptide that can be used as an ingredient of a therapeutic agent for malignant neoplasms, having an activity to induce Th cells specific to the polypeptide from CD4-positive T cells and/or an activity to produce cytokines in such Th cells or Sur/Th cells. The activity to produce cytokines in Th cells specific to the polypeptide or Survivin in each polypeptide described above can be confirmed by stimulating the Th cells with the polypeptide and measuring the produced cytokines by various known methods. For example, the production of interferon γ (INF-γ) can be readily measured and confirmed by using commercially available ELISA kits from BD Biosciences or the like.

To each polypeptide described above which is one aspect of the present invention, as long as the amino acid sequence constituting the polypeptide is contained, for example, His-Tag widely used as a tag sequence useful in separation and purification of proteins, an appropriate linker sequence, and an amino acid sequence of a marker protein such as GFP can be further added. Alternatively, labeled compounds such as biotin can also be added to each polypeptide. Therefore, even a polypeptide comprising an amino acid sequence in which any amino acid residue used for the purpose of other than producing cytokines in Th cells and Sur/Th cells specific to the polypeptide and inducing the cells from CD4-positive T cells is added to the amino acid sequence constituting the polypeptide which is one aspect of the present invention, and a polypeptide in which an appropriate labeled compound is added to the polypeptide of the present invention are still within the scope of the present invention as long as they have an activity to produce cytokines in the cells or they have an epitope that induces specific Th cells from CD4-positive T cells.

The polypeptide of the present invention can be produced as a recombinant protein by applying various known gene recombination techniques to DNA encoding the polypeptide. Typically, the polypeptide may be produced by synthesizing the DNA encoding the polypeptide of the present invention by using an appropriate DNA synthesizer, constructing an expression vector that expresses the polypeptide of the present invention by appropriately selecting or combining various techniques described in reference books in the art such as Sambrook et al., Molecular Cloning: A Laboratory Manual, 2nd edition (Cold Spring Harbor Laboratory Press, 1989), and transforming an appropriate host cell such as E. coli by the expression vector. In the production, as mentioned above, various operations, such as addition of His-tag, used in the production of a recombinant polypeptide can be applied.

The polypeptide of the present invention can also be chemosynthetically produced using an amino acid modified by various protecting groups as a raw material. Methods for organochemically synthesizing a polypeptide without using a gene or a host cell are well known to those skilled in the art. For example, "Jikken Kagaku Koza (Courses in Experimental Chemistry) 16, 5th edition, Yukikagobutsu-no-Gosei (Synthesis of Organic Compounds) IV" (Saburo Aimoto et al., The Chemical Society of Japan) or the like describes various methods for chemical synthesis of a polypeptide, by any of which methods the polypeptide of the present invention can be synthesized. The polypeptide can also be synthesized by using a commercially available apparatus commonly referred to as a peptide synthesizer.

By incubation with antigen-presenting cells and CD4-positive T cells under appropriate conditions, the polypeptide described above can induce the CD4-positive T cells to Th cells. Thus, the present invention also provides a method for inducing Th cells specific to the above-described polypeptide and/or Survivin by incubating in vitro antigen-presenting cells expressing HLA class II molecules, CD4-positive T cells, and the above-described polypeptide. In incubation, in addition to IL-2, one or more of IFN-γ, IL-12, and anti-IL-4 antibodies are preferably added, under which conditions, Th1 cells can be induced which produces IFN-γ and produces IL-4 little.

Any antigen-presenting cell, as mentioned above, can be used in this method as long as the cell expresses HLA class II molecules on its surface, examples of which include B cell, macrophage, monocyte and non-proliferative transfectant as well as dendritic cell, but are not limited thereto. As for incubation, the above-described polypeptide, antigen-presenting cells, and CD4-positive T cells may be simultaneously incubated, or after the polypeptide of the present invention and the antigen-presenting cells are incubated, they may be incubated together with the CD4-positive T cells. The conditions of the incubation of the peptide of the present invention, the antigen-presenting cells expressing HLA class II molecules on their surface, and the CD4-positive T cells, as mentioned above, can be determined according to the incubation conditions in a common method by which the desired antigen is presented by the antigen-presenting cells via the HLA class II molecules and mature Th cells specific to the antigen is induced from CD4-positive T cells, e.g., the above method described in Tim et al.

According to the method of the present invention, Sur/Th cells can be induced and cultured in vitro by collecting antigen-presenting cells and CD4-positive T cells from a patient and incubating these cells and the polypeptide of the present invention. It is expected that return of the Sur/Th cells induced by this method into the patient can activate the immune system of the patient him/herself and cause regression of tumor cells.

The polypeptide of the present invention, by administering it to an appropriate animal such as a rabbit, can induce in the animal antibodies that can specifically recognize Survivin. Such antibodies can specifically detect presence of cells expressed by Survivin, i.e., presence of cancer cells, and therefore can be utilized in efficient diagnosis of malignant neoplasms.

The therapeutic agent for malignant neoplasms of the present invention may contain tumor antigens and Th cells specific to the tumor-specific antigen; it may also contain, to the extent that their actions are not inhibited, various excipients commonly used for formulation of drugs, other pharmaceutically active ingredients or the like. In particular, the therapeutic agent for malignant neoplasms of the present invention is preferably in the form of a buffer solution or a liquid medium that can stably retain the tumor antigens and the Th cells specific to the tumor-specific antigens.

Non-limiting examples of the buffer solution include a neutral buffered saline or a phosphate-buffered saline. The buffer solution may further contain saccharides such as glucose, mannose, sucrose, dextran, and mannitol, proteins, amino acids, antioxidants, bacteriostatic agents, chelating agents (e.g., EDTA or glutathione), adjuvants (e.g. aluminum hydroxide), osmoregulatory agents, suspensions, thickening agents, and/or preservatives.

Although the therapeutic agent for malignant neoplasms of the present invention is preferably in the form of a mixture of tumor antigens and Th cells specific to the tumor-specific antigens, the agent may also be in the form of so-called a kit in which the tumor antigens and the Th cells specific to the tumor-specific antigens, which can be administered in admixture when used, are stored separately.

The present invention will now be described in more detail by way of examples. However, the present invention is not limited to these examples.

EXAMPLES

<Example 1> Identification of SU18

1) Synthesis of Peptide

From the N terminus to C terminus of Survivin, a total of 25 types (referred to as SU1 to SU27) of 19 to 20-amino acid residue peptide (Table 1) having an overlapping sequence of 7 to 8 amino acids at the C terminus and/or N terminus were designed, for example, a peptide composed of 1st to 20th amino acid sequence of Survivin-2B (SEQ ID NO:56), a peptide composed of 8th to 27th amino acid sequence thereof, and a peptide composed of 14th to 34th amino acid sequence thereof, each of which was chemically synthesized.

TABLE 1

| MIX1 | SU1 | MGAPTLPPAWQPFLKDHRIS | Sequence No. 1 |
| | SU2 | PAWQPFLKDHRISTFKNWPF | Sequence No. 2 |
| | SU3 | LKDHRISTFKNWPFLEGCA | Sequence No. 3 |
| | SU4 | FKNWPFLEGCACTPERMAEA | Sequence No. 4 |
| | SU5 | EGCACTPERMAEAGFIHCP | Sequence No. 5 |
| MIX2 | SU6 | PERMAEAGFIHCPTENEPDL | Sequence No. 6 |
| | SU7 | GFIHCPTENEPDLAQCF | Sequence No. 7 |
| | SU8 | PTENEPDLAQCFFCFKELE | Sequence No. 8 |
| | SU9 | DLAQCFFCFKELEGWEPD | Sequence No. 9 |
| | SU10 | FFCFKELEGWEPDDDPIG | Sequence No. 10 |
| MIX3 | SU11 | ELEGWEPDDDPIGPGTVAYA | Sequence No. 11 |
| | SU12 | DDDPIGPGTVAYACNTSTLG | Sequence No. 12 |
| | SU13 | GTVAYACNTSTLGGRGG | Sequence No. 13 |
| | SU14 | NTSTLGGRGGRITREEHK | Sequence No. 14 |
| | SU15 | GGRGGRITREEHKKHS | Sequence No. 15 |
| MIX4 | SU16 | RITREEHKKHSSGCAFL | Sequence No. 16 |
| | SU18 | EHKKESSGCAFLSVKKQFE | Sequence No. 17 |
| | SU20 | GCAFLSVKKQFEELTLGEF | Sequence No. 18 |
| | SU21 | VKKQFEELTLGEFLKLDRER | Sequence No. 19 |
| | SU22 | LTLGEFLKLDRERAKNKIAK | Sequence No. 20 |
| MIX5 | SU23 | KLDREKAKNKIAKETNNKKK | Sequence No. 21 |
| | SU24 | KNKIAKETNNKKKEFEETAK | Sequence No. 22 |
| | SU25 | TNNKKKETEEETAKKVRRAIE | Sequence No. 23 |
| | SU26 | EFEETAKKVRRAIEQLA | Sequence No. 24 |
| | SU27 | AKKVRRAIEQLAAMD | Sequence No. 25 |

In addition, five types of peptide mixtures (MIX1 to MIX5) composed of five peptides were prepared in the order from SU1 to SU27 (SU17 and SU19 were retired), for example, the peptide mixture of SU1 to SU5, the peptide mixture of SU6 to SU10, etc.

2) Preparation of Monocyte-Derived Dendritic Cell and CD4-Positive T Cell

Peripheral blood mononuclear cells (hereinafter referred to as PBMC) were separated from peripheral blood of healthy human whose HLA genotype is HLA-DRB1*0101/HLA-DRB1*0901, using Ficoll (Ficoll-Paque PLUS; GE Healthcare) layer method. PBMCs ($2\times10^6$ cells/well) were plated on a 24-well plate and cultured in a 5% human serum-containing medium (1 mL of 5% human serum in AIM-V) supplemented with recombinant IFN-γ (final concentration of 10 ng/mL) at 37° C. in a $CO_2$ incubator. Two hours later, the resultant was treated with mitomycin C (MMC, Kyowa Hakko) for 45 minutes to inactivate the PBMC. The remaining adherent PBMCs after washing the MMC were referred to as monocyte-derived antigen-presenting cells (PBMC-Ad). Further, CD4-positive T cells were obtained from non-adherent PBMCs (PBMC-nonAd) obtained in induction of PBMCs-Ad using Easy Sep (VERITAS).

3) Establishment of Th Cell Group Comprising Sur/Th Cell Using Synthetic Peptide Co-culture of the PBMCs-Ad prepared in this Example 2) and CD4-positive T cells ($1\times10^6$ cells/well) was started in the presence of the peptide in which five Survivin overlapping peptides prepared in this Example 1) were mixed (MIX1 to MIX5, final concentration of 10 μg/mL) in 1 mL of 5% human serum in AIM-V in a $CO_2$ incubator at 37° C.

After seven days from the start of the co-culture, autologous CD4-positive T cells during the culturing were restimulated using the PBMCs-Ad treated with recombinant IFN-γ as on the first day and the peptides MIX1 to MIX5. After a further two days, recombinant IL-2 was added to a final concentration of 10 U/mL. Further, on Day 14 from the start of the co-culture, the second restimulation was performed on the PBMCs-Ad prepared by the same treatment as on Day 7 and on the autologous CD4-positive T cells cultured for 14 days. Furthermore, after 21 days from the start of the co-culture, the same restimulation as on Day 14 was repeated.

The cells were collected, and in a 96-well U-bottom plate (BD Biosciences) with 200 μL of 5% human serum in AIM-V, each of MIX1, MIX2, MIX3, MIX4, and MIX5 (10 g/mL) was added to the PBMCs ($1\times10^5$ cells/well) and the Th cell group ($4\times10^4$ cell/well) comprising Sur/Th cells previously stained with PE-labeled anti-CD4 antibodies, and the resultants were co-cultured in a $CO_2$ incubator at 37° C. for 2 hours. Thereafter 4 μL of brefeldine A 500 μg/mL (BFA; Sigma, Ayrshire) was added and the resultants were further co-cultured for 4 hours. The cells were collected, and 200 μL of Fixation and Permeabilization solution (BD Biosciences) was added thereto. After being left to stand at room temperature for 20 minutes, the resultant was washed with 0.5% BSA/PBS. FITC-labeled IFN-γ antibodies were added to the resultant, which was stained at room temperature for 15 minutes. The resultant was washed with 0.5% BSA/PBS, and a fluorescence signal was incorporated thereinto using flowcytometry (FACS Calibur, BD Biosciences). By using CellQuest™ (BD Biosciences), 3-colour analysis was performed. The results are shown in FIG. 1.

As shown in FIG. 1, a Th cell group comprising Sur/Th cells which react specifically with MIX4 was obtained.

4) Identification of Polypeptide

The polypeptide was identified by using the Th cell group obtained in this Example 3) comprising Sur/Th cells which react specifically with MIX4.

In a 96-well U-bottom plate (BD Biosciences) with 200 μL of 5% human serum in AIM-V, each of SU16, SU18, SU20, SU21, and SU22 was added, to a final concentration of 10 g/mL, to the PBMCs (1×10$^5$ cells/well) and the Th cell group (4×10$^4$ cell/well) previously stained with PE-labeled anti-CD4 antibodies, the cell group comprising the above-described Sur/Th cells which react specifically with cells using MIX4. The resultants were co-cultured in a $CO_2$ incubator at 37° C. for 2 hours. Thereafter 4 μL each of brefeldine A 500 μg/mL (BFA; Sigma, Ayrshire) was added and the resultants were further co-cultured for 4 hours. The cells were collected, and 200 μL of Fixation and Permeabilization solution (BD Biosciences) was added thereto. After being left to stand at room temperature for 20 minutes, the resultant was washed with 0.5% BSA/PBS. FITC-labeled IFN-γ antibodies were added to each resultant, which was stained at room temperature for 15 minutes. The resultant was washed with PBS containing 0.5% BSA, and a fluorescence signal was incorporated thereinto using flowcytometry (FACS Calibur, BD Biosciences). By using Cell-Quest™ (BD Biosciences), 3-colour analysis was performed. The results are shown in FIG. 2.

Figure 2:
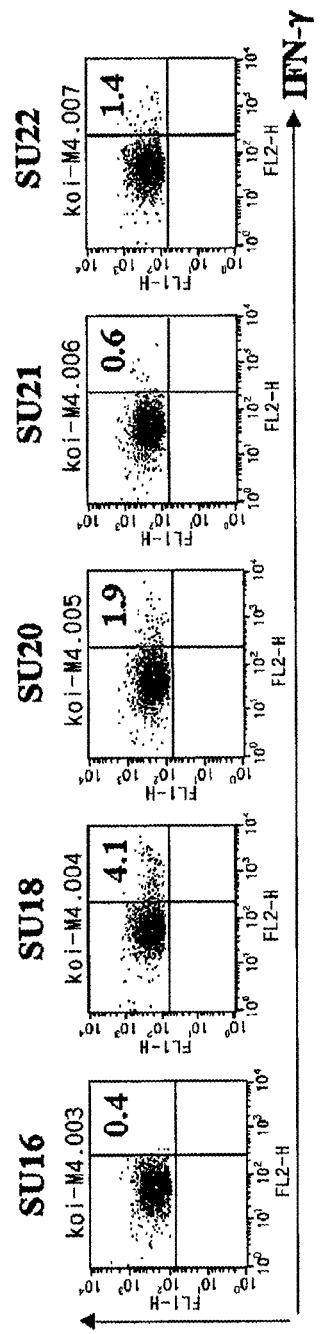
FIG. 2 shows the results of the intracellular staining showing the measurements of the production of INF-γ by Sur/Th cells where each of the polypeptides SU16 to SU22 was added to the group of cells comprising the Sur/Th cells induced from a human whose HLA genotype is HLA-DRB1*0101/HLA-DRB1*0901. In the figure, the ordinate indicates the CD4 expression level and the abscissa the INF-γ expression level.

As shown in FIG. 2, the observation of the cells that antigen-specifically express IFN-γ in the cells supplemented with SU18 confirmed that SU18 was a polypeptide having epitopes presented by HLA class II molecules specific to Survivin.

<Example 2> Examination of HLA-DRB1*0101-Restricted SU18 Recognition Site

1) Confirmation of HLA-Restrictivity

HLA-restrictivity for SU18 was confirmed by using inhibitory antibodies and the Th cell group obtained in Example 1-4) comprising Sur/Th cells which react specifically with SU18.

In a 96-well U-bottom plate (BD Biosciences) with 200 μL of 5% human serum in AIM-V, each of anti-HLA-DP antibodies (Serotech), anti-HLA-DQ antibodies (Serotech) and anti-HLA-DR antibodies (BD Biosciences) was added, to a final concentration of 5 μg/mL, to the PBMCs (1×10$^5$ cells/well) and the above-described Th cell group (5×10$^4$ cell/well) comprising Sur/Th cells which react specifically with SU18. The resultants were co-cultured in the presence of SU18 peptides in a $CO_2$ incubator at 37° C. for 24 hours. After the culturing, the IFN-γ contained in the culture supernatant was measured by using an ELISA kit (BD Biosciences). The results are shown in FIG. 3.

Figure 3:
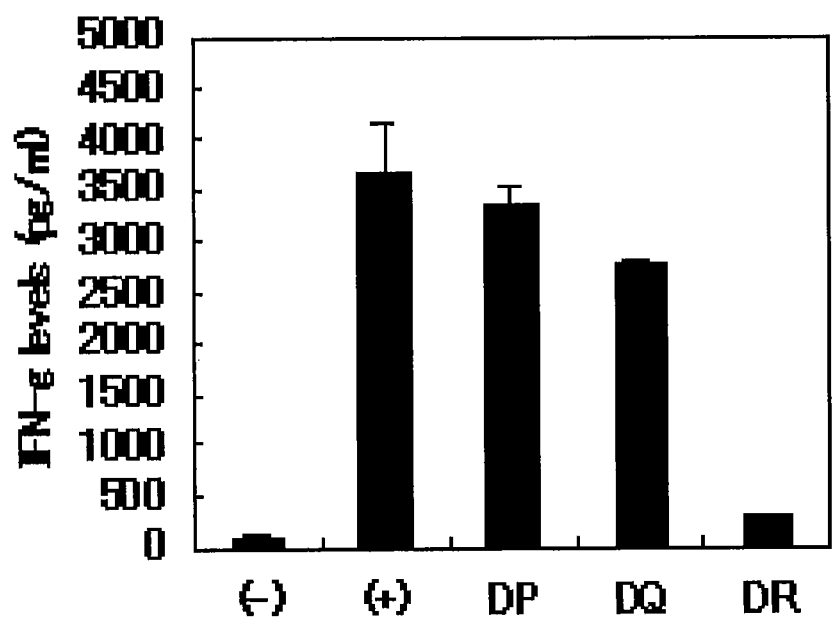
FIG. 3 shows the results of the measurements by ELISA of the production of INF-γ by Sur/Th cells where each of the anti-HLA-DP antibodies, anti-HLA-DQ antibodies, and anti-HLA-DR antibodies was added to the group of cells comprising the Sur/Th cells induced from a human whose HLA genotype is HLA-DRB1*0101/HLA-DRB1*0901. In the figure, the ordinate indicates the production amount of IFN-γ (IFN-g)

As shown in FIG. 3, the inhibition of IFN-γ production by the anti-HLA-DR antibodies confirmed that SU18 was restricted by HLA-DR.

2) Confirmation of HLA-DR-Restrictivity

Since the HLA genotype of the healthy individual whose peripheral blood was taken in Example 1-2) was HLA-DRB1*0101 and HLA-DRB1*0901, HLA-DR-restrictivity was confirmed by using allogeneic antigen-presenting cells to the Th cell group obtained in Example 1-4) comprising Sur/Th cells which react specifically with SU18.

Each of SU18 (cognate) and control peptides (irrelevant) was added, to a final concentration of 10 μg/mL, to allogeneic PBMCs (1×10$^5$ cells/well) whose HLA genotypes are HLA-DRB1*1201/HLA-DRB1*1405, HLA-DRB1*0410/HLA-DRB1*1201, HLA-DRB1*0405/HLA-DRB1*0901, HLA-DRB1*0401/HLA-DRB1*0901, HLA-DRB1*0101/HLA-DRB1*0802, and HLA-DRB1*0101/HLA-DRB1*0101. After 2-hour treatment, each resultant was co-cultured with the above-described Th cell group (5×10$^1$ cell/well) comprising Sur/Th cells which react specifically with SU18 in a 96-well U-bottom plate (BD Biosciences) with 200 μL of 5% human serum in AIM-V in a $CO_2$ incubator at 37° C. for 24 hours. After the culturing, the IFN-γ contained in the culture supernatant was measured by using an ELISA kit (BD Biosciences). The results are shown in FIG. 4.

Figure 4:
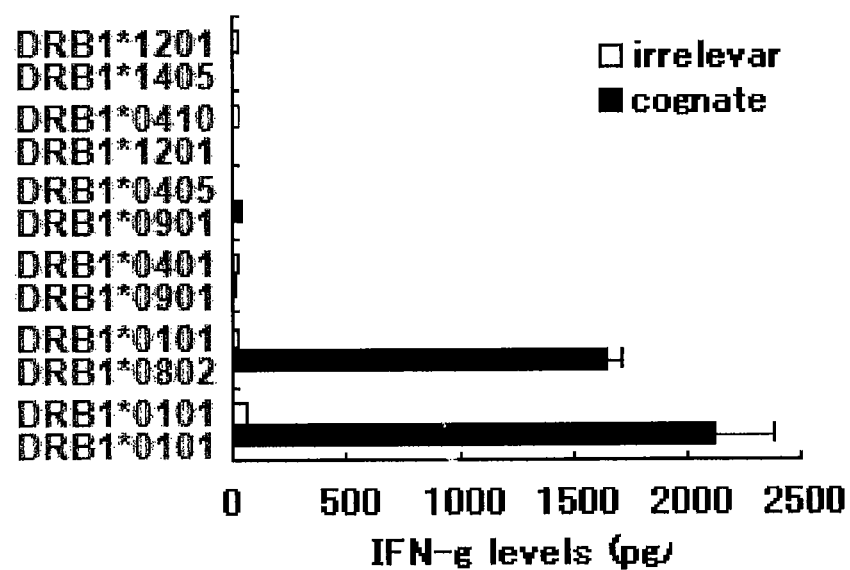
FIG. 4 shows the results of the measurements by ELISA of the production of INF-γ by Sur/Th cells where SU18 (cognate) was added to the group of cells comprising the Sur/Th cells induced from a human whose HLA genotype is HLA-DRB1*0101/HLA-DRB1*0901 and control peptides (irrelevant) were added to allogeneic PBMCs, each HLA genotype of which is HLA-DRB1*1201/HLA-DRB1*1405, HLA-DRB1+0410/HLA-DRB1*1201, HLA-DRB1*0405/HLA-DRB1*0901, HLA-DRB1*0401/HLA-DRB1*0901, HLA-DRB1*0101/HLA-DRB1*0802, and HLA-DRB1*0101/HLA-DRB1*0101. In the figure, the ordinate indicates the each HLA genotype of PBMCs used as antigen-presenting cells and the abscissa indicates the production amount of IFN-γ (IFN-g)

As shown in FIG. 4, from the fact that IFN-γ was produced when the PBMC whose HLA genotype is HLA-DRB1*0101/HLA-DRB1*0802 and HLA-DRB1*0101/HLA-DRB1*0101 was used, SU18 was confirmed to be restricted by HLA-DRB1*0101 among HLA-DR.

3) Confirmation of Recognition Site in Partially Deleted SU18

The recognition site in partially deleted SU18 was confirmed by using the Th cell group obtained in Example 1-4) comprising Sur/Th cells which react specifically with SU18 and the overlapping peptides T1 to T11 shown in Table 2, which are peptides for stimulation.

TABLE 2

| | | |
|---|---|---|
| T1 | EHKKHSSGCAFL | Sequence No. 26 |
| T2 | FEKKHSSGCAFLS | Sequence No. 27 |
| T3 | EHKKHSSGCAFLSV | Sequence No. 28 |
| T4 | EHKKESSGCAFLSVK | Sequence No. 29 |
| T5 | HKKHSSGCAFLSVKK | Sequence No. 30 |
| T6 | KKHSSGCAELSVKKQ | Sequence No. 31 |
| T7 | HSSGCAFLSVKKQF | Sequence No. 32 |
| T8 | HSSGCARSVKKQFE | Sequence No. 33 |
| T9 | SSGCAFLSVKKQFE | Sequence No. 34 |
| T10 | SGCAFLSVKKQFE | Sequence No. 35 |
| T11 | GCAFLSVKKQFE | Sequence No. 36 |

In a 96-well U-bottom plate (BD Biosciences) with 200 μL of 5% human serum in AIM-V, each of the overlapping peptides T1 to T11 was added, to a final concentration of 10 g/mL, to the PBMCs (1×10$^5$ cells/well) and the above-described Th cell group (5×10$^4$ cell/well) comprising Sur/Th cells which react specifically with SU18. The resultants were co-cultured in a $CO_2$ incubator at 37° C. for 24 hours. After the culturing, the IFN-γ contained in the culture supernatant was measured by using an ELISA kit (BD Biosciences). The results are shown in FIG. 5.

Figure 5:
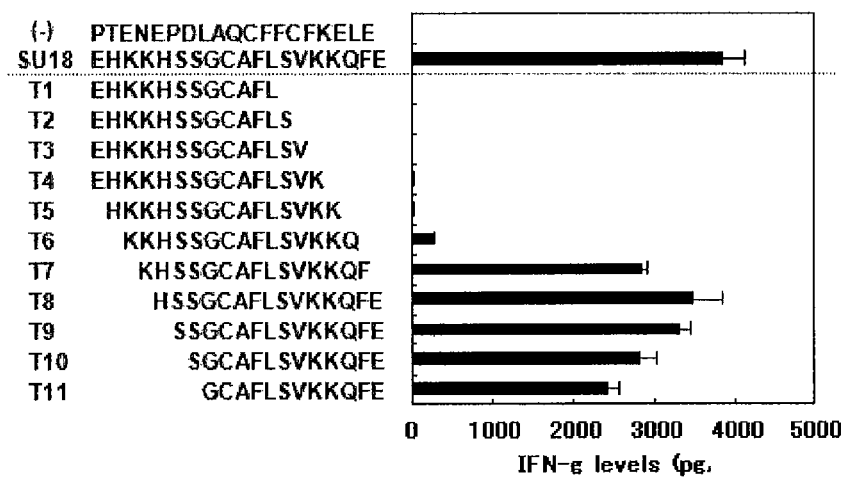
FIG. 5 shows the results of the measurements by ELISA of the production of INF-γ by Sur/Th cells where each of the polypeptides T1 to T11 was added to the Sur/Th cell induced from a human whose HLA genotype is HLA-DRB1*0101. In the figure, the ordinate indicates amino acid sequence of polypeptide added and the abscissa indicates the production amount of IFN-γ (IFN-g)

As shown in FIG. 5, from the fact that IFN-γ was produced and antigen-specific reaction was observed when the overlapping peptide used was T6 (peptide in which the first two amino acids from each of the N and C terminus of SU18 were deleted), T7 (peptide in which the first one amino acid from the C terminus of SU18 and the first three amino acids from the N terminus of SU18 were deleted), T8 (peptide in which the first four amino acids from the N terminus of SU18 were deleted), T9 (peptide in which the first five amino acids from the N terminus of SU18 were deleted), T10 (peptide in which the first six amino acids from the N terminus of SU18 were deleted), and T11 (peptide in which the first seven amino acids from the N terminus of SU18 were deleted), it was confirmed that at least the peptide comprising the peptide of SEQ ID NO:37, GCA-FLSVKKQ (G represents glycine; C cysteine; A alanine; F phenylalanine; L leucine; S serine; V valine; K lysine; and Q glutamine) was able to induce Survivin-specific Sur/Th cells.

<Example 3> Examination of HLA-DRB1*1201/HLA-DRB1*1502-Restricted SU18 Recognition Site 1) Establishment of Th Cell Group Comprising Sur/Th Cells By the 28-day co-culture according to the method described in Example 1-2) and 3), a Th cell group comprising Sur/Th cells was prepared from peripheral blood of a healthy individual whose HLA genotype is HLA-DRB1*1201/HLA-DRB1*1502. Further, to establish a single cell group, a 96-well U-bottom plate was provided with the culture containing 200 µL of the complex medium of human serum and fetal calf serum (2.5% human serum, 2.5% fetal calf serum in AIM-V), PBMCs-Ad ($5\times10^4$ cells/well), recombinant IL-2 (final concentration of 20 U/mL), recombinant IL-7 (final concentration of 10 ng/mL), and phytohemagglutinin (PHA, SEIKAGAKU Co., final concentration of 5 µg/mL). The Th cell group (1 cell/well) was added thereto and the resultant was co-cultured in a $CO_2$ incubator at 37° C.

After 14 days from the start of the co-culture, the wells which showed blast transformation of the cells were scaled up into a 48-well plate with 500 µL of 5% fetal calf serum in AIM-V. Thereafter, restimulation was performed with the PBMCs-Ad pulsed with SU18 at 1-week intervals to obtain Sur/Th cell clones.

2) Confirmation of Recognition Site in Partially Deleted SU18

The recognition site in partially deleted SU18 was confirmed by the ELISPOT assay described below using the Sur/Th cell clones prepared in 1) of this Example 3 and the peptides for stimulation, T1 to T10 shown in Table 3.

TABLE 3

| T1 | EHKKHSSGCAFL | Sequence No. 26 |
| --- | --- | --- |
| T2 | ERKKHSSGCAFLS | Sequence No. 27 |
| T3 | EHKKHSSGCAFLSV | Sequence No. 28 |
| T4 | EHKKHSSGCAFLSVK | Sequence No. 29 |
| T5 | HKKHSSGCAFLSVKK | Sequence No. 30 |
| T6 | KKHSSGCAFLSVKKQ | Sequence No. 31 |
| T7 | KHSSGCAFLSVKKQF | Sequence No. 32 |
| T8 | HSSGCAFLSVKKQFE | Sequence No. 33 |
| T9 | SSGCAFLSVKKQFE | Sequence No. 34 |
| T10 | SGCAFLSVKKQFE | Sequence No. 35 |
| T11 | GCAFLSVKKQFE | Sequence No. 36 |

The ELISPOT assay was performed by using an ELISPOT plate (MAHA S4510, Millipore) and an ELISPOT kit (Mabtech, Nacka). According to the method of using the kit, specifically-induced Th cells and T-APCs were cultured on the ELISPOT plate coated with anti-human IFN-γ antibodies (clone name 1-D1K, mAb) at a concentration of 2 g/mL in the presence of sufficient amount of antigen peptides. After 20 hours from the start of the culture, the culture supernatant was washed away with the washing solution (0.05% Tween 20/PBS). The biotinylated anti-human IFN-γ antibodies (mAb) at a concentration of 0.2 µg/mL was further added to the plate, and the resultant was allowed to react at 4° C. for 16 hours. After the resultant was washed again with the washing solution above, each well was filled with 100 µL of PBS/streptavidin-AP solution (the kit above) and allowed to react at room temperature for 1 hour. Then, the supernatant was washed away with the washing solution above and the resultant was filled with BCIP/NBT-Bule Liquid substrate solution (Sigma). After 10-minute reaction, the resultant was washed with distilled water to stop the reaction. After completion of the reaction, the plate was dried and then the measurements were made by using CTL Immuno-Spot Plate Reader (Cellular Technology). The results are shown in FIG. 6.

Figure 6:
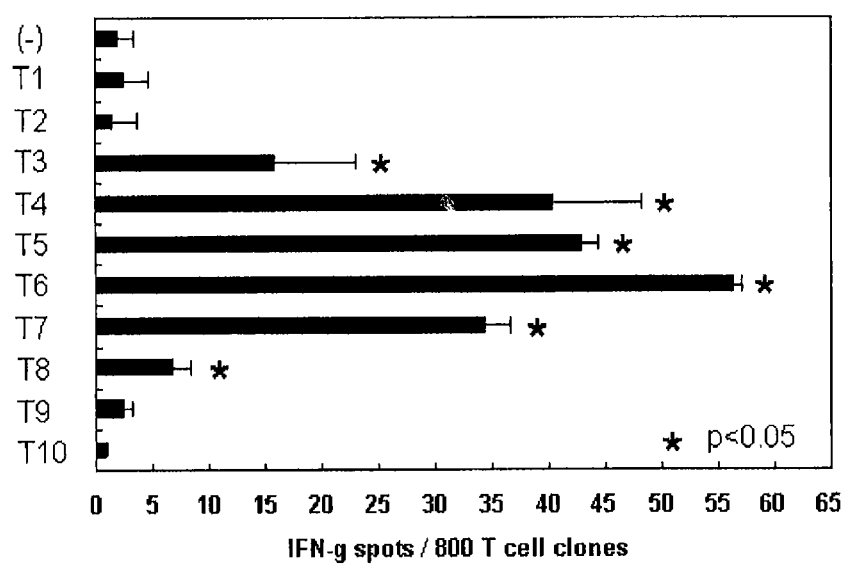
FIG. 6 shows the results of the measurements by the ELISPOT assay for the INF-γ (IFN-g)-producing cell numbers in Sur/Th cells where each of the polypeptides T1 to T10 was added to the Sur/Th cells induced from a human whose HLA genotype is HLA-DRB1*1201/HLA-DRB1*1502.

As shown in FIG. 6, antigen-specific reaction was observed in T3 (peptide in which the first five amino acids from the C terminus of SU18 were deleted) and T8 (peptide in which the first four amino acids from the N terminus of SU18 were deleted). Hence, it was confirmed that SU18 was able to induce Survivin-specific Sur/Th cells even with deletion of the first four amino acids from the N terminus or the first five amino acids from the C terminus. Also, it became clear that SU18 was a polypeptide which has immunotherapeutic effect not only in patients whose HLA genotype is HLA-DRB1*0101/HLA-DRB1*0901 but also in those whose HLA genotype is HLA-DRB1*1201/HLA-DRB1*1502.

<Example 4> Examination of HLA-DQB1*0601-Restricted SU18 Recognition Site

1) Confirmation of HLA-Restrictivity

CD4-positive T cells were prepared from the peripheral blood of healthy individual Y whose HLA genotype is HLA-DQB1*0302/HLA-DQB1*0601 by the same technique as that used in Example 1-2) and a Th cell group comprising Sur/Th cells which react specifically with SU18 was obtained by the same technique as that used in Example 1-3) and 4). HLA-restrictivity for SU18 was confirmed by using inhibitory antibodies and this Sur/Th cell group which reacts specifically with SU18.

In a 96-well U-bottom plate (BD Biosciences) with 200 µL of 5% human serum in AIM-V, each of anti-HLA-DP antibodies (Serotech), anti-HLA-DQ antibodies (Serotech) and anti-HLA-DR antibodies (BD Biosciences) was added, to a final concentration of 5 µg/mL, to the PBMCs ($1\times10^5$ cells/well) and the above-described Th cell group ($5\times10^4$ cell/well) comprising Sur/Th cells which react specifically with SU18. The resultants were co-cultured in the presence of SU18 peptides in a $CO_2$ incubator at 37° C. for 24 hours. After the culturing, the IFN-γ contained in the culture supernatant was measured by using an ELISA kit (BD Biosciences). The results are shown in FIG. 7.

Figure 7:
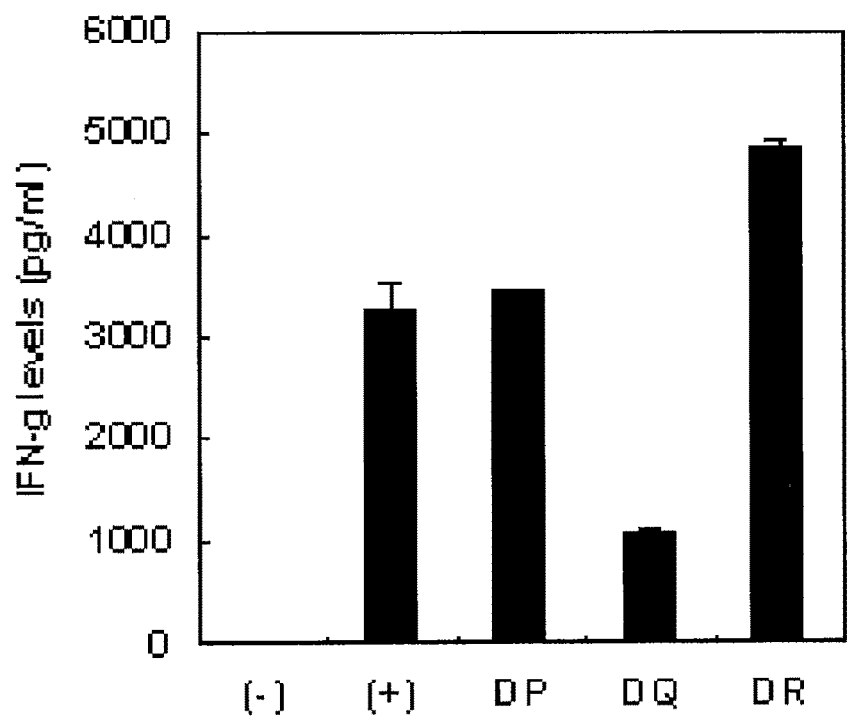
FIG. 7 shows the results of the measurements by ELISA of the production of INF-γ by Sur/Th cells where each of the anti-HLA-DP monoclonal antibody (mAb), anti-HLA-DQ mAb, and anti-HLA-DR mAb was added to the Sur/Th cells induced from a human whose HLA genotype is HLA-DQB1*0302/HLA-DQB1*0601. In the figure, the ordinate indicates the production amount of IFN-γ (IFN-g)

As shown in FIG. 7, the inhibition of IFN-γ production by the anti-HLA-DQ antibodies confirmed that SU18 was restricted by HLA-DQ.

2) Confirmation of HLA-DQ-Restrictivity

HLA-DQ-restrictivity was confirmed by using allogeneic antigen-presenting cells to the Th cell group obtained in this Example 1) comprising Sur/Th cells which react specifically with SU18.

Each of SU18 (cognate) and control peptides (irrelevant) was added, to a final concentration of 10 µg/mL, to allogeneic PBMCs ($1\times10^5$ cells/well) whose HLA genotypes are HLA-DQB1*0301/HLA-DQB1*0302, HLA-DQB1*0401/HLA-DQB1*0602, HLA-DQB1*0302/HLA-DQB1*0401, and HLA-DQB1*0301/HLA-DQB1*0601. After 2-hour treatment, each resultant was co-cultured with the above-described Th cell group (5×10⁴ cell/well) comprising Sur/Th cells which react specifically with SU18 in a 96-well U-bottom plate (BD Biosciences) with 200 μL of 5% human serum in AIM-V in a $CO_2$ incubator at 37° C. for 24 hours. After the culturing, the IFN-γ contained in the culture supernatant was measured by using an ELISA kit (BD Biosciences). The results are shown in FIG. 8.

Figure 8:
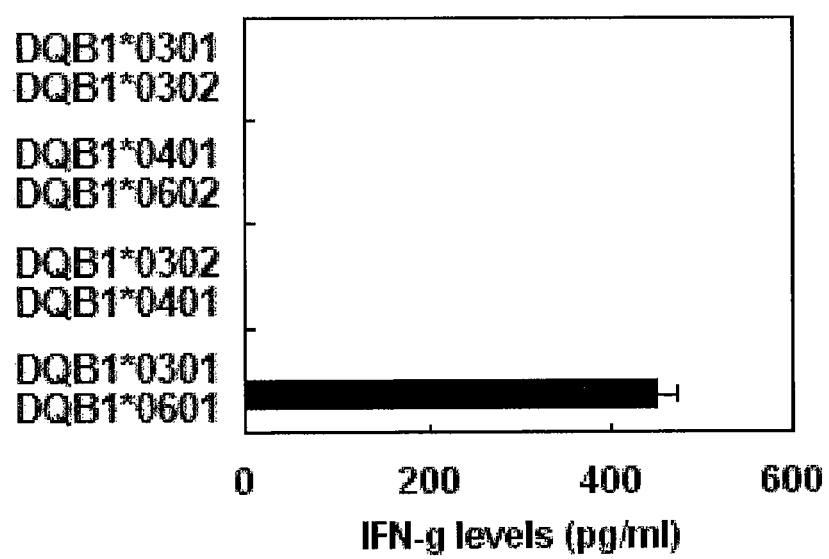
FIG. 8 shows the results of the measurements by ELISA of the production of INF-γ by Sur/Th cells where SU18 (cognate) or control (irrelevant) peptides were added to the cells comprising the Sur/Th cells induced from a human whose HLA genotype is HLA-DQB1*0302/HLA-DQB1*0601 with allogeneic PBMCs, each HLA genotype of which is HLA-DQB1*0301/HLA-DQB1*0302, HLA-DQB1*0401/HLA-DQB1*0602, HLA-DQB1*0302/HLA-DQB1*0401, and HLA-DQB1*0301/HLA-DQB1*0601. In the figure, the ordinate indicates amino acid sequence of polypeptide added and the abscissa indicates the production amount of IFN-γ (IFN-g)

As shown in FIG. 8, from the fact that IFN-g was not produced when the PBMCs whose HLA genotype is HLA-DQB1*0301/HLA-DQB1*0302 and HLA-DQB1*0302/HLA-DQB1*0401 was used and that IFN-γ was produced when the PBMC whose HLA genotype is HLA-DQB1*0301/HLA-DQB1*0601 was used, SU18 was confirmed to be restricted by HLA-DQB1*0601 among HLA-DQ.

3) Confirmation of Recognition Site in Partially Deleted SU18

The recognition site in partially deleted SU18 was confirmed by using the Th cell group obtained in 1) of this Example 4 comprising Sur/Th cells which react specifically with SU18 and the overlapping peptides T1 to T10 shown in Table 3, which are peptides for stimulation.

In a 96-well U-bottom plate (BD Biosciences) with 200 μL of 5% human serum in AIM-V, each of the overlapping peptides T1 to T10 was added, to a final concentration of 10 μg/mL, to the PBMCs (1×10⁵ cells/well) and the above-described Th cell group (5×10⁴ cell/well) comprising Sur/Th cells which react specifically with SU18. The resultants were co-cultured in a $CO_2$ incubator at 37° C. for 24 hours. After the culturing, the IFN-γ contained in the culture supernatant was measured by using an ELISA kit (BD Biosciences). The results are shown in FIG. 9.

Figure 9:
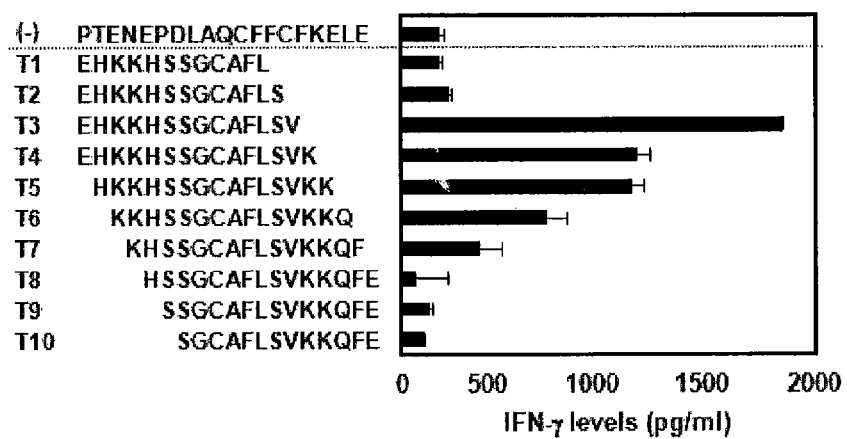
FIG. 9 shows the results of the measurements by ELISA of the production of INF-γ by Sur/Th cells where each of the polypeptides T1 to T10 was added to the Sur/Th cells induced from a human whose HLA genotype is HLA-DQB1*0601. In the figure, the ordinate indicates amino acid sequence of polypeptide added and the abscissa indicates the production amount of IFN-γ (IFN-g)

As shown in FIG. 9, from the fact that IFN-γ was produced and antigen-specific reaction was observed when the overlapping peptide used was T3 (peptide in which the first five amino acids from the C terminus of SU18 were deleted), T4 (peptide in which the first four amino acids from the C terminus of SU18 were deleted), T5 (peptide in which the first three amino acids from the C terminus of SU18 and the first one amino acid from the N terminus of SU18 were deleted), T6 (peptide in which the first two amino acids from each of the N and C terminus of SU18 were deleted), and T7 (peptide in which the first one amino acid from the C terminus of SU18 and the first three amino acids from the N terminus of SU18 were deleted), it was confirmed that at least the peptide comprising the peptide of SEQ ID NO: 57, KHSSGCAFLSV (K represents lysine; H histidine; S serine; G glycine; C cysteine; A alanine; F phenylalanine; L leucine; and V valine) was able to induce a Survivin-specific Sur/Th cells.

4) Confirmation of Recognition Site in Partially Substituted SU18

The recognition site in partially substituted SU18 was confirmed by using the Th cell group obtained in this Example 1) comprising Sur/Th cells which react specifically with SU18 and the partially substituted peptides S1 to S17, peptides for stimulation shown in Table 4, in which each amino acid of SU18 was substituted with alanine (A) or glycine (G).

In a 96-well U-bottom plate (BD Biosciences) with 200 μL of 5% human serum in AIM-V, each of the partially substituted peptides S1 to S17 was added, to a final concentration of 10 μg/mL, to the PBMCs (1×10⁵ cells/well) and the above-described Th cell group (5×10⁴ cell/well) comprising Sur/Th cells which react specifically with SU18. The resultants were co-cultured in a $CO_2$ incubator at 37° C. for 24 hours. After the culturing, the IFN-γ contained in the culture supernatant was measured by using an ELISA kit (BD Biosciences). The results are shown in FIG. 10.

Figure 10:
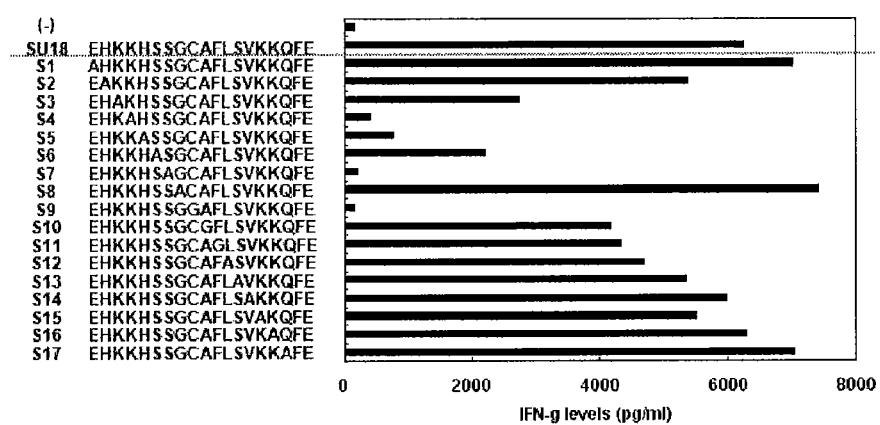
FIG. 10 shows the results of the measurements by ELISA of the production of INF-γ by Sur/Th cells where each of the polypeptides S1 to S17 was added to the Sur/Th cells induced from a human whose HLA genotype is HLA-DQB1*0601. In the figure, the ordinate indicates amino acid sequence of polypeptide added and the abscissa indicates the production amount of IFN-γ (IFN-g).

As shown in FIG. 10, it was confirmed that IFN-γ was hardly produced when the partially substituted peptide used was S4 (peptide in which lysine, the fourth from the N terminus of SU18, was substituted with alanine), S5 (peptide in which histidine, the fifth from the N terminus of SU18, was substituted with alanine), S7 (peptide in which serine, the seventh from the N terminus of SU18, was substituted with alanine), and S9 (peptide in which cysteine, the ninth from the N terminus of SU18, was substituted with glycine). That is, it was confirmed that at least the peptide of SEQ ID NO:55, XXXKHXSXCXXXXXXXXXX (Xaa represents any amino acid; K lysine; H histidine; S serine; and C cysteine) was able to induce Survivin-specific Sur/Th cells.

What is claimed:

1. A method for inducing production of interferon γ (INF-γ) in a patient in need thereof, comprising administering to the patient a polypeptide in an effective amount, wherein the patient has a HLA genotype of HLA-DBR1*0101 or HLA-DQB1*0601, and wherein the polypeptide consists of the amino acid sequence of SEQ ID NO: 17 or a variation thereof,
    a) wherein the variation consists of the amino acid sequence identical to the amino acid sequence of SEQ ID NO: 17 except that one to five amino acids at the C terminus of the amino acid sequence of SEQ ID NO: 17 are deleted;
    b) wherein the variation consists of the amino acid sequence identical to the amino acid sequence of SEQ ID NO: 17 except that one to seven amino acids at the N terminus of the amino acid sequence of SEQ ID NO: 17 are deleted;
    c) wherein the variation consists of the amino acid sequence identical to the amino acid sequence of SEQ ID NO: 17 except that any one of amino acid residues at positions of 1-3, 6, 8 and 12-18 of the amino acid sequence of SEQ ID NO: 17 is substituted with alanine; or
    d) wherein the variation consists of the amino acid sequence identical to the amino acid sequence of SEQ ID NO: 17 except that an amino acid residue at position 10 or 11 of the amino acid sequence of SEQ ID NO: 17 is substituted with glycine.

2. The method of claim 1, wherein the polypeptide consists of the amino acid sequence of SEQ ID NO: 17.

3. The method of claim 1, wherein the polypeptide consists of a variation of the amino acid sequence of SEQ ID NO: 17, wherein the variation consists of the amino acid sequence identical to the amino acid sequence of SEQ ID NO: 17 except that one to five amino acids at the C terminus of the amino acid sequence of SEQ ID NO: 17 are deleted.

4. The method of claim 1, wherein the polypeptide consists of a variation of the amino acid sequence of SEQ ID NO: 17, wherein the variation consists of the amino acid sequence identical to the amino acid sequence of SEQ ID NO: 17 except that one to seven amino acids at the N terminus of the amino acid sequence of SEQ ID NO: 17 are deleted.

5. The method of claim 1, wherein the polypeptide consists of a variation of the amino acid sequence of SEQ ID NO: 17, wherein the variation consists of the amino acid sequence identical to the amino acid sequence of SEQ ID NO: 17 except that any one of amino acid residues at positions of 1-3, 6, 8 and 12-18 of the amino acid sequence of SEQ ID NO: 17 is substituted with alanine.

6. The method of claim 1, wherein the polypeptide consists of a variation of the amino acid sequence of SEQ ID NO: 17, wherein the variation consists of the amino acid sequence identical to the amino acid sequence of SEQ ID NO: 17 except that one or an amino acid residue at position 10 or 11 of the amino acid sequence of SEQ ID NO: 17 is substituted with glycine.

7. A method for inducing a Th cell specific to Survivin, comprising incubating in vitro a polypeptide, an antigen-presenting cell and a CD4-positive T cell, wherein the polypeptide consists of the amino acid sequence of SEQ ID NO: 17 or a variation thereof,
    a) wherein the variation consists of the amino acid sequence identical to the amino acid sequence of SEQ ID NO: 17 except that one to five amino acids at the C terminus of the amino acid sequence of SEQ ID NO: 17 are deleted;
    b) wherein the variation consists of the amino acid sequence identical to the amino acid sequence of SEQ ID NO: 17 except that one to seven amino acids at the N terminus of the amino acid sequence of SEQ ID NO: 17 is deleted;

c) wherein the variation consists of the amino acid sequence identical to the amino acid sequence of SEQ ID NO: 17 except that any one or more of amino acid residues at positions of 1-3, 6, 8 and 12-18 of the amino acid sequence of SEQ ID NO: 17 is substituted with alanine; or d) wherein the variation consists of the amino acid sequence identical to the amino acid sequence of SEQ ID NO: 17 except that an amino acid residue at position 10 or 11 of the amino acid sequence of SEQ ID NO: 17 is substituted with glycine.

8. The method of claim 7, wherein the polypeptide consists of the amino acid sequence of SEQ ID NO: 17.

9. The method of claim 7, wherein the polypeptide consists of a variation of the amino acid sequence of SEQ ID NO: 17, wherein the variation consists of the amino acid sequence identical to the amino acid sequence of SEQ ID NO: 17 except one to five amino acids at the C terminus of the amino acid sequence of SEQ ID NO: 17 are deleted.

10. The method of claim 7, wherein the polypeptide consists of a variation of the amino acid sequence of SEQ ID NO: 17, wherein the variation consists of the amino acid sequence identical to the amino acid sequence of SEQ ID NO: 17 except that one to seven amino acids at the N terminus of the amino acid sequence of SEQ ID NO: 17 are deleted.

11. The method of claim 7, wherein the polypeptide consists of a variation of the amino acid sequence of SEQ ID NO: 17, wherein the variation consists of the amino acid sequence identical to the amino acid sequence of SEQ ID NO: 17 except that any one of amino acid residues at positions of 1-3, 6, 8 and 12-18 of the amino acid sequence of SEQ ID NO: 17 is substituted with alanine.

12. The method of claim 7, wherein the polypeptide consists of a variation of the amino acid sequence of SEQ ID NO: 17, wherein the variation consists of the amino acid sequence identical to the amino acid sequence of SEQ ID NO: 17 except that an amino acid residue at position 10 or 11 of the amino acid sequence of SEQ ID NO: 17 are substituted with glycine.

* * * * *